US00PP33006P2

(12) United States Plant Patent
Hansen

(10) Patent No.: US PP33,006 P2
(45) Date of Patent: Apr. 27, 2021

(54) ***PHLOX* PLANT NAMED 'MAJESTIC MAGENTA'**

(50) Latin Name: ***Phlox* hybrid**
Varietal Denomination: Majestic Magenta

(71) Applicant: Hans A Hansen, Zeeland, MI (US)

(72) Inventor: Hans A Hansen, Zeeland, MI (US)

(73) Assignee: Walters Gardens Inc., Zeeland, MI (US)

( * ) Notice: Subject to any disclaimer, the term of this patent is extended or adjusted under 35 U.S.C. 154(b) by 0 days.

(21) Appl. No.: 16/974,098

(22) Filed: Sep. 30, 2020

(51) Int. Cl.
*A01H 5/02* (2018.01)
*A01H 6/70* (2018.01)

(52) U.S. Cl.
USPC ..... Plt./320

(58) Field of Classification Search
USPC ..... Plt./320
See application file for complete search history.

*Primary Examiner* — Susan McCormick Ewoldt

(57) ABSTRACT

A unique cultivar of Hybrid Creeping *Phlox* plant named 'Majestic Magenta' characterized by vigorous, dense, low spreading, multi-stemmed, winter-hardy habit with short, bright green, linear to awl-shaped leaves. Flowering begins in late-April and continuing for up to four weeks, in cooler weather conditions, on heavily-branched peduncles and completely cover the plant in peak season. Petals have a small notch and the tips and newly opened flowers and mature flowers remain a rich dark-pink color. The new plant is able to withstand dry conditions once established, and the foliage stays clean and resists mildew. The new plant is especially suitable for the landscape as a potted plant and in the garden as a specimen or en masse.

1 Drawing Sheet

Botanical classification: *Phlox* hybrid.
Variety denomination: 'Majestic Magenta'.

STATEMENT REGARDING PRIOR DISCLOSURES UNDER 37 CFR 1.77(b)(6)

The first non-enabling disclosure of the claimed plant, in the form of a photograph and brief description on a website operated by Walters Gardens, Inc. on Feb. 2, 2020. Subsequently, the new plant was advertised in the "Walters Gardens 20-21 Catalog" by Walters Gardens, Inc. released on May 20, 2020. The claimed plant was first sold to the public on Mar. 16, 2020 by Walters Gardens, Inc., who obtained the plant and all information relating thereto, from the inventor. No plants of *Phlox* 'Majestic Magenta' have been sold to the public in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to a new and distinct cultivar of Hybrid Creeping *Phlox* plant known as *Phlox* 'Majestic Magenta' and will be referred to hereafter by its cultivar name, 'Majestic Magenta', or the "new plant". The new plant was hybridized by the inventor at a wholesale perennial nursery in Zeeland, Mich. on May 9, 2014 as a cross between *Phlox subulata* 'Scarlet Flame' (not patented) as the female or seed parent and *Phlox douglasii* 'Cracker Jack' (not patented) as the male or pollen parent. The new plant passed initial evaluation on the spring of 2017 and was assigned the breeder code 14-415-2 through the remaining evaluation process. 'Majestic Magenta' was first asexually propagated by stem cuttings in the greenhouses at the same nursery in Zeeland, Mich. in the summer of 2017. The unique characteristics of the new plant have been found to be reproducible and stable in successive generations of asexually propagated and the resultant plants have been found to be identical to the original selection.

BRIEF SUMMARY OF THE PLANT

*Phlox* 'Majestic Magenta' is unique from all other Hybrid Spring *Phlox* known to the inventor. The nearest comparison plants known to the inventor include: 'Rocky Road Magenta' U.S. Plant Pat. No. 31,485, 'Rose Quartz' copending U.S. Plant patent application Ser. No. 16/974,228, 'Plumtastic' U.S. Plant Pat. No. 28,896. 'Rocky Road Magenta', has flowers of magenta-purple with a small dark eye. 'Rose Quartz' is more vigorous spreading and has slightly a taller habit with rose-pink flower color that lightens with maturity. 'Plumtastic' has flowers of violet-pink with purple markings near the eye, and the flower initially has a light, near-white center that darkens to the same violet-pink at maturity.

The female parent, 'Scarlet Flame', has narrower petals with deeper scarlet flowers with darker spotting near the eye, and the habit is taller and more vigorously spreading. The male parent, 'Crackerjack' is slower spreading and shorter in habit and has smaller flowers that are more red with slight orangish tint.

*Phlox* 'Majestic Magenta' differs from and all other *Phlox* known to the inventor in the following repeatedly observed traits in combination:

1. Vigorous plants of dense, slowly-spreading habit, spreading by rooting stems, producing short, clean, glabrous, bright-green, narrow leaves;
2. Multiple heavily-branched stems produce branched panicles;

3. Flower beginning in late-April and continuing for up to four weeks, in cool conditions, nearly completely covering plant at peak flowering;
4. Flowers of rich dark-pink and with small notches at the tip of the petals;
5. Plant is able to withstand dry conditions once established.

BRIEF DESCRIPTION OF THE DRAWINGS

The photographs of the new plant demonstrate the unique traits of *Phlox* 'Majestic Magenta' and the overall appearance of the plant at three-years-old growing in a full-sun trial beds in Zeeland, Mich. The colors are as accurate as reasonably possible with color reproductions. Variation in ambient light spectrum, source and direction may cause the appearance of minor variation in color.

DETAILED BOTANICAL DESCRIPTION

Figure 1:
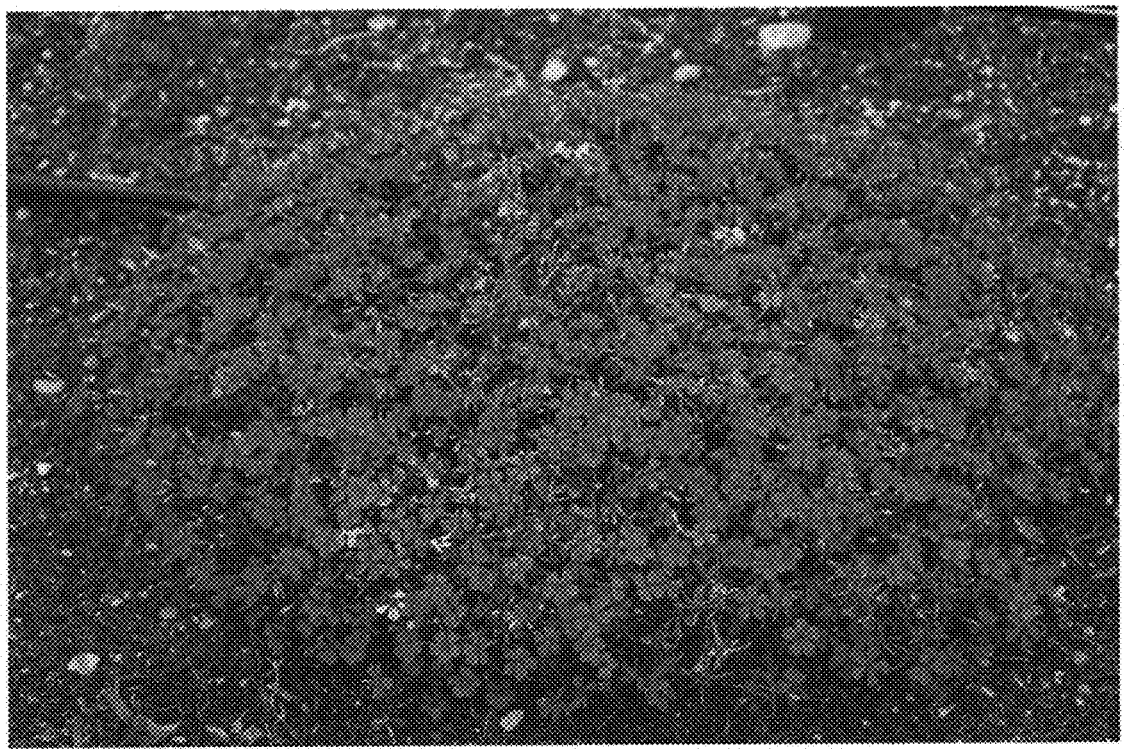
FIG. 1 shows a landscape habit view of the new plant in peak flower.
Figure 2:
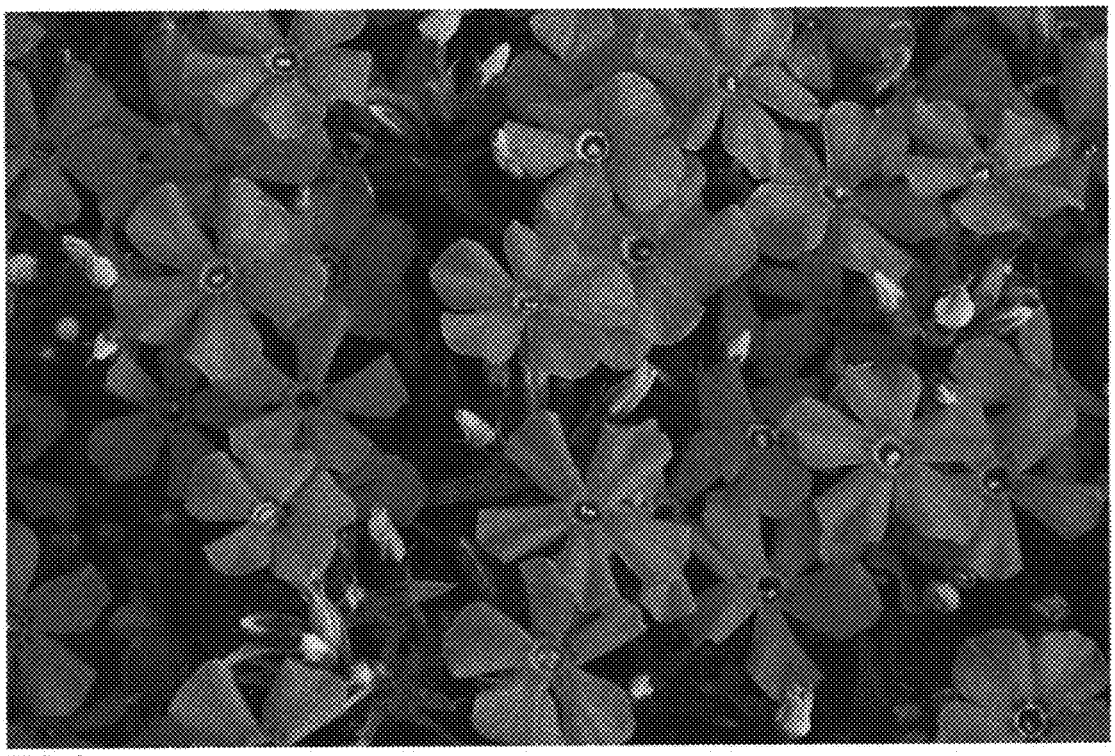
FIG. 2 shows a close-up of the flowers and buds.

The following descriptions and color references are based on the 2015 edition of The Royal Horticultural Society Colour Chart except where common dictionary terms are used. *Phlox* 'Majestic Magenta' has not been observed under all possible environments. The phenotype may vary slightly with different growing environments such as temperature, light, fertility, soil pH, moisture and maturity levels, but without any change in the genotype. The following observations and size descriptions are based on three-year-old plants in gallon containers grown in a partially shaded greenhouse and also in the full-sun trial garden of a wholesale perennial nursery in Zeeland, Mich. with supplemental fertilizer and water as needed.

Botanical classification: *Phlox* hybrid;

Parentage: Female or seed parent is *Phlox subulata* 'Scarlet Flame', male or pollen parent is *Phlox douglasii* 'Crackerjack';

Plant habit: Winter-hardy, evergreen herbaceous perennial; short, dense, producing about 50 to 75 stiff, highly-branched prostrate stems; foliage to 13.5 cm tall and 58.0 cm wide, average 13.0 cm tall and 52.0 cm wide; flowering to 13.5 cm tall and 60.0 cm wide;

Propagation: Stem cuttings; rooting in about 3 weeks;

Time to produce finished crop in 3.8 liter pots: About 8 to 12 weeks; moderately vigorous;

Root: Fibrous and freely branching; color creamy white to tan depending on soil type;

Leaves: Simple; opposite proximally, whorled distally; linear to subulate; apex narrowly acute to mucronulate; base truncate, clasping; margin entire and micro-ciliolate; glabrous both adaxial and abaxial, matte adaxial and lustrous abaxial; about 16.0 mm long by about 2.0 mm wide at base, average about 14.0 mm long and 2.0 mm wide;

Leaf color: Adaxial expanding and mature nearest RHS 138A, abaxial both expanding and mature nearest RHS 138B;

Foliage fragrance: None detected;

Veins: Pinnate; not conspicuous adaxial and abaxial;

Vein color: Same color as surround leaf;

Petiole: Leaves sessile;

Stems: Cylindrical; flexible; wiry; prostrate; highly branching; to about 5.0 mm long and 1.0 mm diameter near base;

Stem color: Color nearest RHS 145A when exposed;

Nodes: Proximally about 5.0 mm apart; distally less than 1.0 mm apart;

Node color: Color nearest RHS 145B;

Inflorescence: Upright to outwardly; about 2.5 cm long and 3.0 cm wide; average of 3 flowers;

Flowers: Perfect; salverform; mostly flat faced; about 15.0 mm across face and 12.0 mm long; with fused corolla tube about 11.0 mm long and 2.0 mm diameter near face; attitude upright to slightly outwardly;

Flower longevity: About 5 days on plant; self-cleaning;

Flower fragrance: Very faintly sweet;

Buds one to two days prior to opening: Narrowly oblanceolate, to narrowly clavate; bluntly acute apex with rounded base; petals implicate; about 14.0 mm long, 5.5 mm long in terminal bulb portion and 8.5 mm long in tube; corolla tube to 1.5 mm diameter, bulb to 2.5 mm diameter;

Bud color: Exposed petal bulb portion nearest RHS 72B; distal tube portion nearest RHS 72C, corolla tube basal 2.0 mm nearest RHS 145C; calyx base nearest RHS 138B, distally nearest RHS 138A with slight blush in high light exposure of nearest RHS N187A;

Petals: Five; obtuse; consisting of limb and basal claw fused into corolla tube; apex rounded, crenulate and shallowly emarginate, cleft to about 0.5 mm deep; limbs not imbricate; margin entire; glabrous adaxial and abaxial;

Petal size: Limb about 8.0 mm long and 7.0 mm wide near middle; tube about 11.0 mm long and 2.0 mm diameter;

Petal color upon opening:

*Adaxial.*—Limb nearest RHS 72A with two faint bars near eye about 0.5 mm long and 0.5 mm wide nearest RHS N79A; proximal 4.0 mm of tube nearest RHS 145C, remaining distal tube portion between RHS 79D and RHS NN155D.

*Abaxial.*—Limb nearest RHS 72B, proximal 1.0 mm of tube nearest RHS 145B, next proximal 2.0 mm nearest RHS 150D, remaining distal tube portion nearest RHS 79C.

Petal color upon maturity:

*Adaxial.*—Limb nearest RHS 72A with two faint bars near eye about 0.5 mm long and 0.5 mm wide nearest RHS N79B; proximal 4.0 mm of tube nearest RHS 145C, remaining distal tube portion between RHS 79D and RHS NN155D.

*Abaxial.*—Limb nearest RHS 72B, proximal 1.0 mm of tube nearest RHS 145B, next proximal 2.0 mm nearest RHS 150D, remaining distal tube portion nearest RHS 79C.

Androecium: Typically five;

*Filaments.*—Typically five, adnate to inner corolla to various heights about 8.0 mm to 11.5 mm from base; free in the distal 1.0 mm long and 0.2 mm in diameter; color nearest RHS NN155D.

*Anther.*—Five; oblong elliptic; dorsifixed; oblong, about 1.5 mm long by 0.5 mm wide; color nearest RHS 16A.

*Pollen.*—Nearly microscopic; color nearest RHS 17A.

Gynoecium: One pistil per flower; 11.0 mm long;

*Style.*—Cylindrical; about 8.0 mm long and 0.3 mm diameter when flower is mature; persistent after flower abscission; color nearest RHS 145C.

*Stigma.*—Bifid to trifid in proximal 1.0 mm long, about 0.3 mm diameter; color between RHS 2C and RHS 2B.

*Ovary.*—Superior; conical; glabrous and lustrous; acute apex and truncate base; about 1.0 mm long and 1.0 mm diameter; color nearest RHS 143A.

Calyx: Campanulate; to about 10.0 mm long and 4.5 mm across at apex;

Sepals: Five; lanceolate; glabrous adaxial and puberulent abaxial; narrowly acute to apiculate apex, fused in basal 5.0 mm; margin entire; matte abaxial, and lustrous adaxial; individually to about 10.0 mm long and 1.0 mm wide at fusion;

Sepal color: Adaxial nearest RHS 138A with margins nearest RHS 196D; abaxial nearest RHS 137C with light blush in high light exposure of nearest RHS N187A;

Peduncle: Glabrous; slightly lustrous; strong, flexible; mostly upright; cylindrical; to about 1.0 mm diameter at base and 2.0 cm long;

Peduncle color: Low light or ventrally nearest RHS 145D; high light or ventrally nearest RHS 145D with moderate blush to nearly solid nearest RHS 187A;

Pedicle: Cylindrical; glabrous; slightly lustrous; flexible; upright to outwardly; variable lengths from about 3.0 mm to 8.0 mm long and 0.7 mm diameter;

Pedicle color: Low light or ventrally nearest RHS 145D; high light or ventrally nearest RHS 145D with moderate blush to solid nearest RHS 187A;

Fruit and seeds: Not observed;

Hardiness and culture: The new plant grows best with full sun, light moisture and deep drainage; hardy to at least from USDA zone 4 through 8;

Disease and pest resistance: *Phlox* 'Majestic Magenta' demonstrates excellent powdery mildew resistance under conditions that would normally show symptoms;

I claim:

1. A new and distinct cultivar of Hybrid Creeping *Phlox* plant named 'Majestic Magenta', as herein described and illustrated.

* * * * *